United States Patent
Mishra et al.

[11] Patent Number: 5,826,586
[45] Date of Patent: Oct. 27, 1998

[54] METHODS FOR PRODUCING MEDICAL IMPLANTS WITH ROUGHENED, PARTICULATE-FREE SURFACES

[75] Inventors: Ajit K. Mishra, Memphis; James A. Davidson, Germantown; Mark A. Hamby, Bartlett, all of Tenn.

[73] Assignee: Smith & Nephew, Inc., Memphis, Tenn.

[21] Appl. No.: 787,656

[22] Filed: Jan. 21, 1997

Related U.S. Application Data

[60] Continuation of Ser. No. 475,893, Jun. 7, 1995, abandoned, which is a division of Ser. No. 405,898, Mar. 17, 1995, abandoned.

[51] Int. Cl.$^6$ .............................. A61B 19/00; A61F 2/02
[52] U.S. Cl. .................. 128/898; 623/11; 623/16; 623/901; 134/7
[58] Field of Search ................... 623/11, 16, 66, 623/901; 128/898; 134/7

[56] References Cited

U.S. PATENT DOCUMENTS

| | | | |
|---|---|---|---|
| 4,617,064 | 10/1986 | Moore et al. | 134/7 |
| 5,057,108 | 10/1991 | Shetty et al. | 606/53 |
| 5,147,466 | 9/1992 | Ohmori et al. | 134/7 |
| 5,226,260 | 7/1993 | Mar et al. | 51/319 |
| 5,236,459 | 8/1993 | Koch et al. | 623/16 |
| 5,251,468 | 10/1993 | Lin et al. | 72/53 |
| 5,258,098 | 11/1993 | Wagner et al. | 156/645 |
| 5,307,594 | 5/1994 | Panchison | 51/310 |
| 5,317,841 | 6/1994 | Cook et al. | 51/321 |
| 5,344,494 | 9/1994 | Davidson et al. | 134/1 |
| 5,607,480 | 3/1997 | Beaty | 623/11 |

FOREIGN PATENT DOCUMENTS

| | | |
|---|---|---|
| 0 602 712 A2 | 6/1994 | European Pat. Off. . |
| WO 94/16836 | 8/1994 | WIPO . |

*Primary Examiner*—Paul B. Prebilic
*Attorney, Agent, or Firm*—Pravel, Hewitt, Kimball & Krieger

[57] ABSTRACT

Many medical implants have roughened surfaces that promote cell, bone or tissue adhesion as well as the adhesion of bone cement, for better affixing of the implants in the body. The roughened surfaces should be free of particulates, such as commonly arise from the blasting of implant surfaces with particulates to produce a desired surface finish. A method of producing implants with implant surfaces free of such particulates is to blast the implant surface with a biocompatible liquid, such as water, under high pressure. Under certain circumstances, a solvent may contain particulates that assist in producing the roughened surface, and the particulates are dissolved, sublimated or vaporized from the implant surface, leaving no particulate residue.

7 Claims, 7 Drawing Sheets

METHODS FOR PRODUCING MEDICAL IMPLANTS WITH ROUGHENED, PARTICULATE-FREE SURFACES

This application is a Continuation of application Ser. No. 08/475,893, filed Jun. 7, 1995, now abandoned which is a Division of application Ser. No. 08/405,898, filed Mar. 17, 1995, now abandoned.

BACKGROUND OF THE INVENTION

1. Field of the Invention

The invention relates to medical implants, of all kinds, with roughened surfaces that promote cell, bone or tissue adhesion as well as the adhesion of bone cement, sometimes used to affix certain implants in place in the body. Further, the roughened surface implants of the invention are free of particulates, such as commonly arise from the blasting of implant surfaces with particulates to produce a desired surface finish.

2. Description of the Related Art

In the final stages of the preparation of medical implants, the implants are sometimes blasted with a solid medium, such as alumina, silica (glass), or silicon carbide, to roughen the surfaces. This roughening process is designed to enhance the attachment of bone, cell, tissue, or bone cement, depending upon the implant application.

Roughened surfaces may advantageously be applied to a variety of medical implants, including orthopedic implants, dental implants, cardiovascular implants, and the like. For orthopedic and dental implants, the rough surface facilitates interlocking of the implant with bone, tissue or bone cement. This tends to minimize micromotion, a phenomenon that results in loosening of the implant. Roughened surfaces on cardiovascular implants promote desirable cell attachment which has been linked with a reduction in thrombus response.

Blasting and shotpeening implants with solid media also introduce residual compressive stresses on the surface of the implants, thereby improving the fatigue strength of the device. To the extent that the surfaces can also be roughened by these treatments, fatigue strength is reduced. Thus, fatigue strength increases with greater residual surface compressive stresses and decreases with increase in surface roughness.

Regardless of the rationale for blasting implant surfaces with particulate solid media, the commonly used blasting process can result in contamination of the implant surface with fragments of the particulates. Typically, the blasting medium is carried by compressed air and is harder than the implant so that fragments of the blasting medium become embedded in or attached to the surface of the implant. Unless this residual debris is removed, it can be released into the body following implantation and cause adverse cell and tissue reactions. Even when the blasting medium is of a biocompatible material, adverse cell and tissue reactions have been observed in the presence of particulate debris. This is known as "particulate disease" and has been observed as being caused by ingestion of these particulates by macrophages which subsequently exhibit a foreign body response and release certain enzymes that cause lysis or death of bone cells. This in turn can lead to loosening of the implant and failure of the surgery. Particulate debris may also potentially migrate into spaces between articulating surfaces of a total hip or knee joint prosthesis thereby causing accelerated three-body abrasive wear. This abrasion process can also increase the generation of polymer or metal debris from the joint prosthesis and further accelerate adverse cell and tissue response. Not only does this tend to reduce the useful life of the implant, which is abraded away, but it also results in inflammation of joints and particulate disease.

There is therefore a perceived need for implants with roughened surfaces that will enhance the attachment of cells, bone, tissue or bone cement, without introducing particulate debris into the body. There is also a need for efficient methods for producing such medical implants.

While the prior art describes surface treatment processes for orthopedic implant devices, none of the art describes implants, or methods of producing implants, meeting these requirements. For example, U.S. Pat. No. 5,057,108 relates to a surface treatment process for stainless steel orthopedic implant devices. In this process, the stainless steel implant is first blasted with stainless steel shot to cold work the surface and introduce residual compressive stresses. The steel shot blasting treatment is then followed by blasting with smaller glass beads, represented as improving the fatigue properties of the surface by cold working those areas not covered by the larger steel shot. It is also represented that glass bead blasting cleans the surface of any residual steel shot that may have transferred to the implant surface. After these two steps, the surface is electropolished and passivated by immersion in nitric acid solution. However, even if the glass beads remove stainless steel contamination, the implant surface may then contain imbedded or loosely attached debris from the glass beading process. Electropolishing or passivation would not remove this cross-contamination particulate debris which would ultimately be released into the body of a patient potentially causing adverse cell reactions.

Similarly, U.S. Pat. No. 5,251,468 describes a method of blasting the surfaces of orthopedic implants with media including calcium phosphate ceramics, phosphate glass compositions, bioabsorbable glass, partially bioabsorbable glass, bioabsorbable ceramics, and partially bioabsorbable ceramics. The purpose of the blasting is to enhance the fatigue and corrosion properties of the implant and to remove residual carbon from porous surfaces of an implant. While it is represented that, because the particles are made of bioactive material they are not a cause for concern when remaining as a residue on the porous surface, it is nevertheless well known that particulate disease has been observed regardless of the nature of the debris. Thus, even the supposedly harmless bioactive blasting materials of this patent can cause particulate disease or accelerated three-body abrasive wear of total joint implants.

U.S. Pat. No. 5,236,459 describes a method in which a high pressure liquid jet is used to form cone shaped cavities in an implant on spacings to provide for intercommunication between the respective cavities. However, in order for these apertures to communicate "below the surface of the implant," significant amounts of material need to be removed and deep cavities formed. This would cause significant reduction in the fatigue strength of the implant.

U.S. Pat. No. 5,258,098 describes a chemical milling process to create an attachment surface for increasing adhesion between two objects or materials. However, the chemical etchants which are used for this purpose are strong acids which are hazardous to work with and create environmental concerns at the time of disposal after use. Further, if any of these acids remain on the implant when it is implanted, they can cause damage to the adjacent bone and tissue.

U.S. Pat. No. 5,226,260 describes a method which includes the step of eroding elastomer from a medical electronic lead using particulate abrasive. However, the patent states that the particulate should be such as to avoid scratching of the embedded metal. The patent does not address how to roughen the surface of metallic and other implants for enhanced bone or bone cement attachment.

International patent application WO 94/16836 is directed toward a method of cleaning roughened or porous-coated medical implant surfaces that contain loosely-adherent debris and particles. The disclosed method involves blasting the surface of the implant with biocompatible particulate solids in a manner which dislodges the debris and particles. This method, however, only cleans the surface and does not itself roughen the surface or produce residual compressive stresses in the surface.

SUMMARY OF THE INVENTION

The invention is directed to a method of forming medical implants, of all kinds, with roughened surfaces for enhanced cell and bone cement attachment, and implants with such surfaces. The implant surfaces may have residual compressive stresses and are free of particulate debris, thereby reducing or eliminating the potential for particulate disease and curtailing the potential for accelerated three-body abrasive wear caused by particulate debris.

The preferred methods for producing medical implants according to the invention include subjecting surfaces of the medical implant to a high pressure jet of a biocompatible liquid. The impact pressure of the solvent on the implant surface should be sufficient to remove machining debris and also roughen the surface for bone, cell, tissue or bone cement adhesion. It may also introduce residual compressive stresses into the surface to enhance fatigue strength.

In alternative embodiments of the preferred method, the biocompatible liquid may include a biocompatible, solid particulate medium, such as non-toxic soluble salts, non-toxic particulate solids that deliquesce, sublimate or vaporize, but that are sufficiently hard to provide an effective impact on the implant surface to create a roughened surface for bone, tissue, cells or bone cement adhesion.

After the implant surface is blasted with the biocompatible liquid containing biocompatible particulate solids described above, the implant may optionally be subjected to ultrasonic cleaning or flushing with a biocompatible liquid medium to remove or dissolve any blasting residue.

Finally, the roughened implant surface may be further treated to provide a chemically passive surface. Such passivation techniques include dipping in solutions of nitric acid, or passivating by immersion in solutions of non-aggressive oxyanions, as detailed in U.S. Pat. No. 5,211,663, which is hereby fully incorporated by reference. The process parameters used during the blasting process may be adjusted depending upon whether roughening the surface for enhanced cement, bone, tissue or cell attachment is the primary objective, or improving the fatigue strength by introducing residual compressive stresses is the primary objective. If roughening the surface is the primary objective, more aggressive blasting methods, e.g., higher blasting pressure, greater duration of blasting and/or smaller blasting nozzle distance, may be employed. If improvement in fatigue strength is the primary objective, roughening of the surface should be minimized by judicious selection of the operating variables since increased surface roughness causes reduction in fatigue strength. If solid blasting media are being used, this may involve using more spherical media and/or denser media which would resist fragmentation and minimize roughening of the substrate.

DESCRIPTION OF THE PREFERRED EMBODIMENTS

Figure 1:
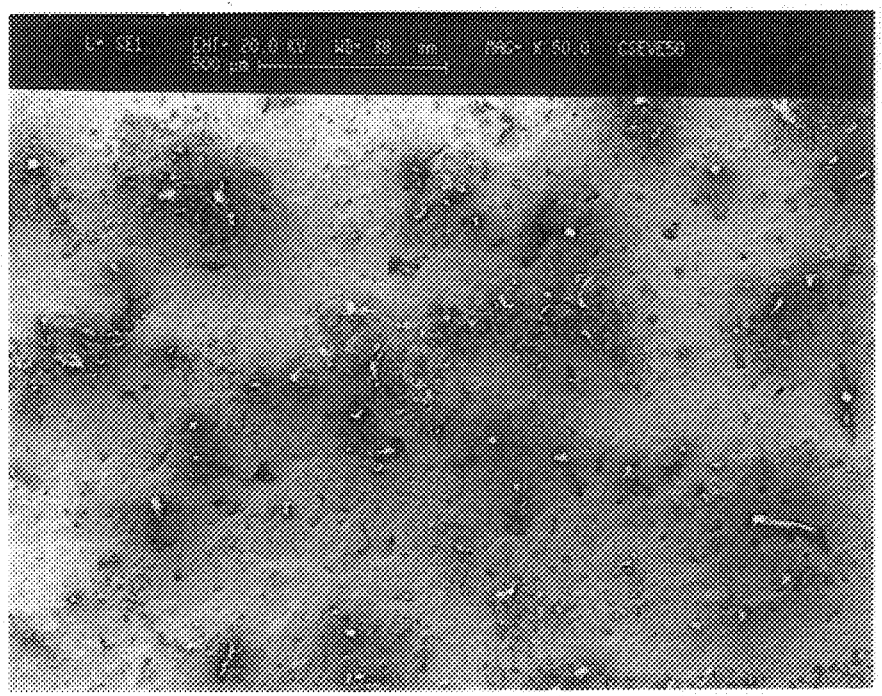
FIG. 1 is a photomicrograph of a surface of cobalt-chrome-molybdenum alloy disk (C-7) at 50 times magnification after being hydroblasted with water only.

The roughened surface implants, according to the invention, which are free of particulate debris, are preferably produced by blasting implant surfaces with biocompatible liquids at high pressures. These liquids may further contain soluble, vaporizable, or deliquescable solid particulates. The resultant surfaces are roughened for improved tissue and cell adhesion, and bone cement adhesion, as required. Also, the surfaces may contain residual compressive stresses that enhance the fatigue strength of the implant.

In a preferred embodiment of the methods for producing implants according to the invention, an implant surface is subjected to blasting with pressurized water. The pressure of the water is selected depending upon the hardness of the surface material of the medical implant. Thus, a softer metal, such as aluminum, will require a lower water pressure than a harder metal alloy, such as cobalt-chrome-molybdenum, to produce the same roughness index on the surface. For instance, in order to produce an average surface roughness ($R_a$) of 250 micro-inches on an aluminum implant surface, the water pressure should range from about 10,000 to about 90,000 psi, if the implant is located 0.5 inches distance from the point at which the water exits a jet tip and the traverse-rate (the speed of travel of the spray nozzle) is about 4 inches per second. To produce a cobalt-chrome-molybdenum medical implant of the same roughness, the water pressure should range from about 10,000 to about 90,000 psi, and should be located at a distance of 0.5 inches from the tip of the water jet, and the traverse-rate should be about 100 times lower at 0.04 inches per second. The lower traverse-rate permits blasting of the material for longer periods of time and this is essential due to the greater hardness of Co-Cr-Mo compared to aluminum. The same effect can also be produced by using a higher pressure instead of a lower traverse-rate. This can also be achieved by using a shorter working distance (i.e., the distance between the blasting nozzle and the implant).

Implants, according to the invention, may be produced from a wide range of metals and alloys, including such materials as titanium, cobalt, zirconium, tantalum, niobium, nickel, aluminum, and their alloys, as well as stainless steels. Implants, according to the invention, may also be produced from ceramic and plastics. Some of these metals or alloys are harder than others so that blasting parameters should be adjusted to achieve a desired $R_a$. Therefore, for example, the suitable pressure parameter range can be from about 3,000 psi to about 90,000 psi. The desired $R_a$ is one such that the roughness is high enough to promote attachment of tissue, bone, cells, or bone cement, but low enough to minimize adverse effects on wear and fatigue strength.

One of the blasting parameters that may be varied, according to the invention, is the density of the liquid biocompatible blasting medium. Thus, denser liquids have higher impact on the implant surface and hence are more effective at roughening harder surfaces.

The average surface roughness ($R_a$) and the topography of the roughened surface, may be altered by a judicious selection of operating variables in the hydroblaster. These variables include but are not limited to the blasting pressure, duration of blasting, distance of blasting nozzle from implant surface, the number of blasting passes over a given area, the configuration of the jet-spray (e.g., fan type or orifice type). In the event that particulates are included in the blasting medium to assist in imparting residual compressive stresses to the surface and/or to roughen the surface, then further operating variables such as the size, shape and hardness of the particles used also have a significant effect on the topography of the roughened surface produced. Thus, for instance, particles of larger size and higher hardness will tend to produce greater surface roughening as well as higher residual compressive stresses. More spherical particles would tend to cause less surface roughening and higher residual compressive stresses. Denser particles, which would tend to resist fragmentation, would also have the same effect.

Blasting with either biocompatible liquids or solid particulates in a fluid carrier medium may be accomplished using many different types of spray nozzles, depending upon the type of surface desired. A 0° orifice nozzle directs a stream of the blasting medium at a small area of the workpiece. A 15° fan nozzle directs a fan-type spray of the blasting medium over a larger area of the workpiece. Other types of spray patterns can also be produced by judicious selection of the blasting nozzle. The nozzles may be rotated continuously about their own axis to convert a fan-shaped spray to a cone-shaped spray. The workpiece and/or the spray gun may be subjected to translation, revolution or rotation to ensure uniform blasting of different areas of the workpiece. The spray-gun may be moved horizontally, vertically, or both (to produce a cross-hatch pattern).

The degree and nature of surface roughening produced by the blasting process is measured by a number of parameters. The most commonly used parameter is the average surface roughness, $R_a$. This is a measure of the arithmetic average deviation of the roughness profile from its mean line. Thus this parameter gives equal weight to peaks as well as valleys on the surface. The reduced peak height, $R_{pk}$, is a parameter which is a measure of the number and height of the peaks on the surface. Reduced valley depth, $R_{vk}$, is a measure of the number and depth of the valleys on the surface.

The following examples are illustrative of the invention and are not intended to limit the scope of the invention as described above and claimed hereafter.

EXAMPLE 1

Three materials commonly used in medical implants, wrought (ASTM F 799) cobalt-chrome-molybdenum, Ti-6Al-4V, and aluminum, were selected for subjecting to blasting using various combinations of blasting media and blasting parameters. The hardness of these materials were as follows:

| Material | Hardness (VHN) |
|---|---|
| Aluminum | 107 |
| Ti-6Al-4V | 370 |
| Cobalt-Chrome-Molybdenum (ASTM F 799) | 465 |

(where VHN stands for Vickers Hardness Number)

Disc specimens of each of these materials were blasted at a pressure of 10,000 psi with water as a carrier including salt particles. Other specimens were hydroblasted with water only at a pressure of 36,000 psi. The results are as shown in Table 1.

TABLE 1

| Specimen Number | Specimen Material | Water Pressure (psi) | Media Used | Traverse Rate (ips) | Number of passes | Average Surface Roughness ($R_a$) (micro inches) | Reduced Peak Height ($R_{pk}$) (micro inches) | Reduced Valley Depth ($R_{vk}$) (micro inches) |
|---|---|---|---|---|---|---|---|---|
| A-2 | Aluminum | 10000 | salt | ** | ** | 244 | 222 | 896 |
| A-3 | " | 10000 | salt | ** | ** | 96 | 92 | 459 |
| A-4 | " | 36000 | none | 0.1 | 1 | 816 | 172 | 1126 |
| A-5 | " | 36000 | none | 1 | 1 | 663 | 352 | 154 |
| A-6 | " | 36000 | none | 2 | 1 | 322 | 332 | 540 |
| A-7 | " | 36000 | none | 4 | 1 | 257 | 389 | 228 |
| T-2 | Ti—6Al—4V | 10000 | salt | ** | ** | 33 | 51 | 92 |
| T-3 | " | 10000 | salt | ** | ** | 71 | 14 | 42 |
| T-4 | " | 36000 | none | 0.1 | 1 | 203 | 274 | 336 |
| T-5 | " | 36000 | none | 0.25 | 1 | 193 | 140 | 380 |

TABLE 1-continued

| Specimen Number | Specimen Material | Water Pressure (psi) | Media Used | Traverse Rate (ips) | Number of passes | Average Surface Roughness ($R_a$) (micro inches) | Reduced Peak Height ($R_{pk}$) (micro inches) | Reduced Valley Depth ($R_{vk}$) (micro inches) |
|---|---|---|---|---|---|---|---|---|
| T-7 | " | 36000 | none | 0.33 | 1 | 211 | 143 | 412 |
| T-8 | " | 36000 | none | 0.4 | 1 | 105 | 23 | 437 |
| T-9 | " | 36000 | none | 1 | 1 | 43 | 34 | 31 |
| C-5 | ASTM F799 Co—Cr—Mo | 36000 | none | 0.04 | 1 | 93 | 33 | 516 |
| C-6 | " | 36000 | none | 0.04 | 2 | 244 | 178 | 455 |
| C-7 | " | 36000 | none | 0.04 | 3 | 233 | 241 | 525 |

The salt used here is sodium chloride.
**Manual Operation, procees parameters do not apply
Note:
All tests used a 15° fan jet spray nozzle and a 0.5 inch working distance. All roughness measurements ($R_a$, $R_{pk}$, and $R_{vk}$) were performed using a profilometry trace perpendicular to the direction of travel of the blasting nozzle. The following equipment settings were used: Trace Length = 0.050 inch, Cut-off Length = 0.030 inch, Tracing Speed = 0.012 inch/sec., Phase Correction Filter Activated.

A roughened surface for enhancement of cement or bone attachment was achieved on an aluminum specimen by blasting with salt using water as the carrier medium at 10,000 psi. The roughness ($R_a$) of the surface was 244 micro inches. However, under the same conditions, surface roughness of the Ti-6Al-4V specimens (T-2 and T-3)were considerably lower due to the greater hardness of this material relative to aluminum. It is expected that even higher pressures or harder blasting media would be required to produce a comparable surface roughness on cobalt-chrome-molybdenum disks, which have considerably harder surfaces.

Blasting with water alone was effective to produce an average roughness ($R_a$) of 257 micro inches on the aluminum specimen A-7 using a spray nozzle travel speed of 4.0 inches per second. Lower traverse-rates produced even higher surface roughness values. Since increased roughness tends to cause reduction in fatigue strength, process parameters may be adjusted to insure that the surface produced is not so rough as to cause an unacceptable reduction in fatigue strength in the implant.

Blasting with water at 36,000 psi, without salt, was effective in producing a surface roughness ($R_a$) of 203 micro-inches on a Ti-6Al-4V specimen, T-4. The higher pressure was achievable due to the smaller nozzle useable in the absence of solid blasting media.

Even for the cobalt-chrome-molybdenum disks, which have a high hardness, (465 VHN), blasting with water produced an average roughness ($R_a$) of 233 micro-inches and 244 micro-inches respectively on specimens C-6 and C-7. However, to achieve this roughness, a traverse-rate of 0.04 inch per second was required, along with 2–3 passes of the spray over the surface.

Figure 13:
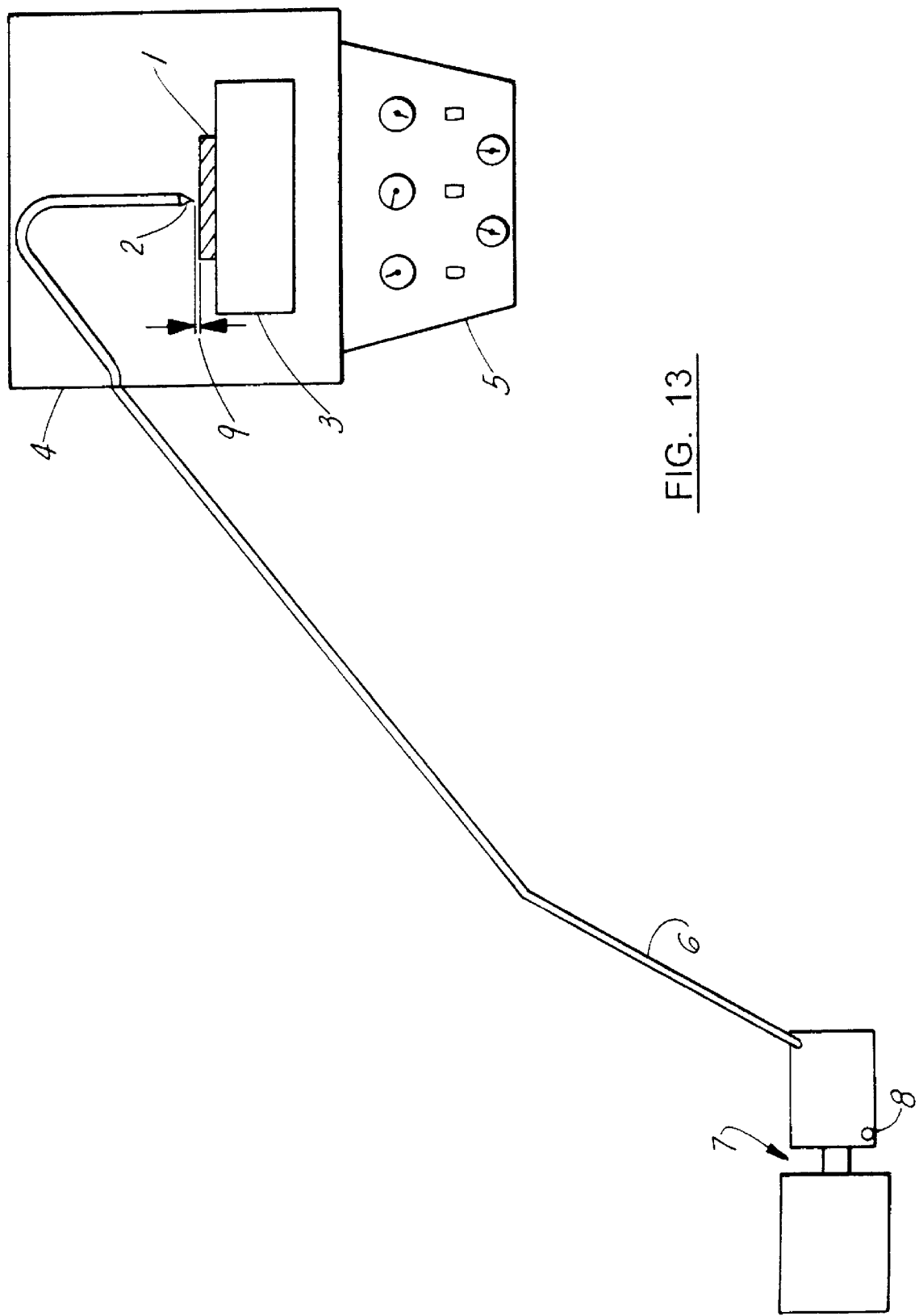
FIG. 13 is a schematic of the equipment used for the invention blasting process.

The equipment used for the water-jet blasting, as well as the salt and water blasting described in Table 1, was manufactured by National Liquid Blasting, Wixom, Mo. A schematic of the equipment is shown in FIG. 13. The equipment includes: a Z-axis adjustable blasting nozzle (2); a X-axis, Y-axis, and rotational fixturing (3); a sonic insulated stainless steel blasting enclosure (4); controls for high pressure liquid supply and position, speed and traverse-rate movements for X-, Y- and Z-axes as well as rotation (5); a regulated high pressure water supply (6); an electric motor driven pump and high pressure manifold (7); and a filtered tap water inlet (8). The working distance (9), the distance between the top surface of the workpiece (1) and the nozzle tip, is typically 0.25 inches with a #5 nozzle.

Figure 2:
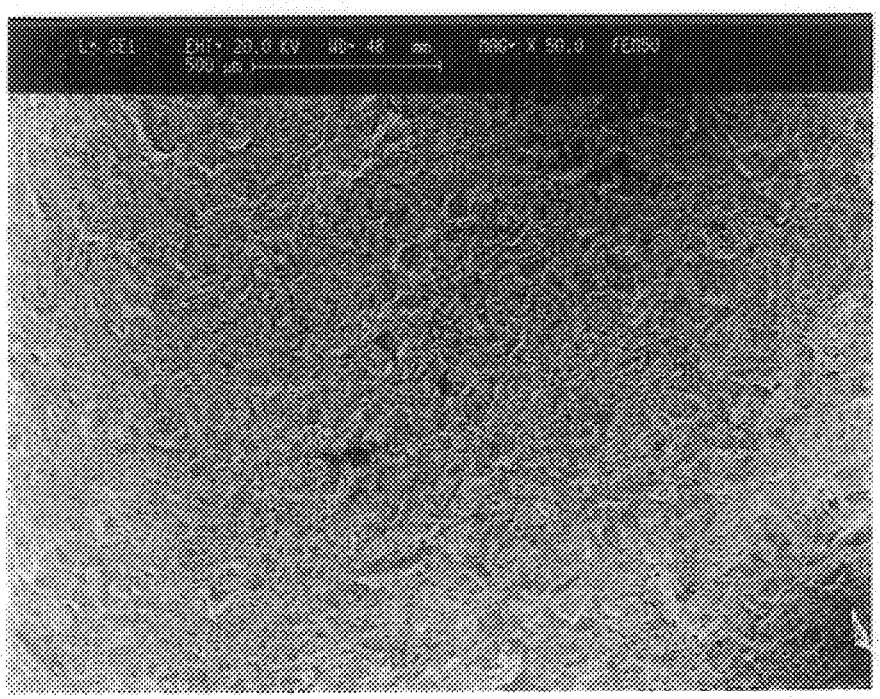
FIG. 2 is a photomicrograph of the surface of cobalt-chrome-molybdenum alloy femoral knee component at 50 times magnification, after blasting with alumina grit.
Figure 3:
FIG. 3 is a photomicrograph at 200 times magnification of a water jet blasted cobalt-chrome-molybdenum alloy disc (C-7).
Figure 4:
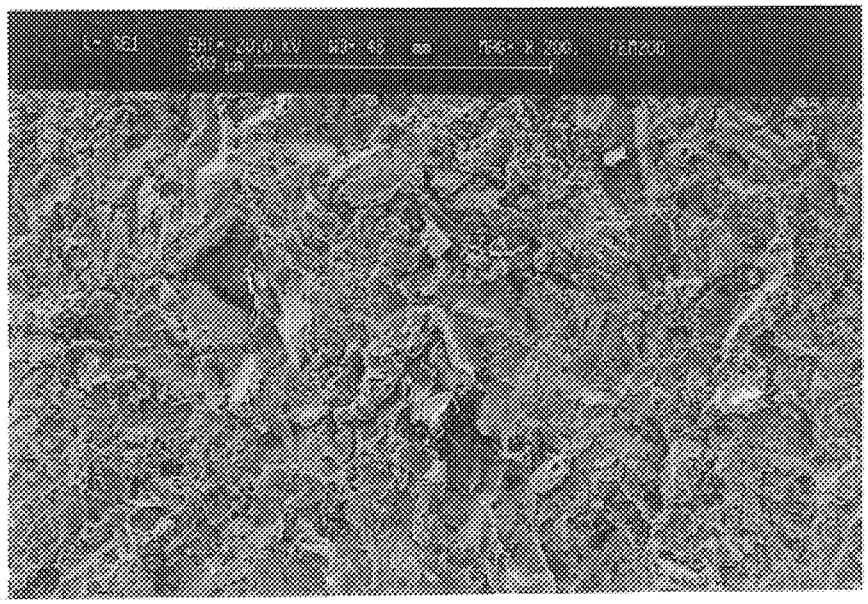
FIG. 4 is a photomicrograph at 200 times magnification of an alumina grit blasted cobalt-chrome-molybdenum knee femoral component.
Figure 5:
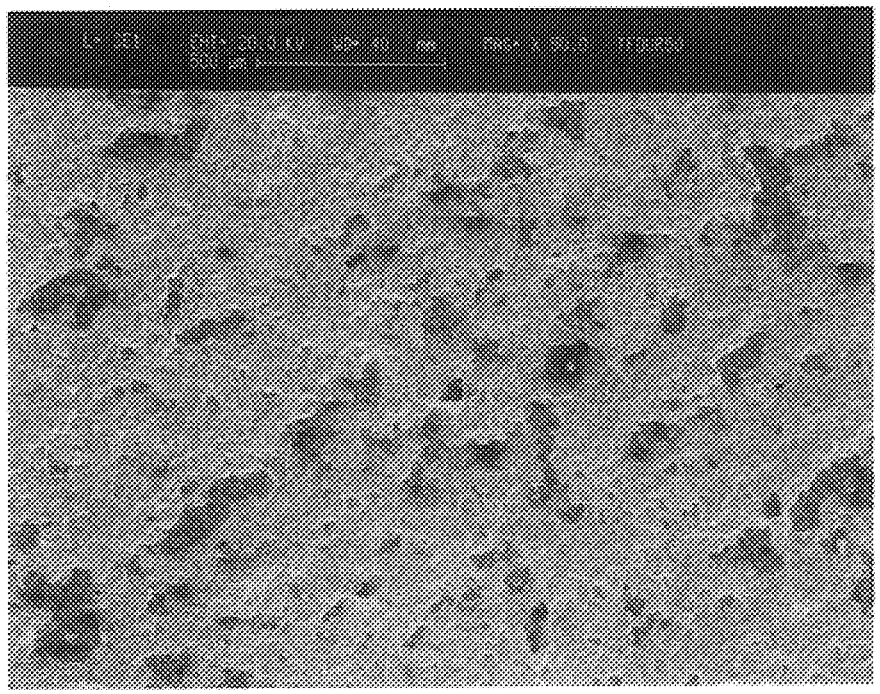
FIG. 5 is a photomicrograph at 50 times magnification of the surface of a water jet blasted Ti-6Al-4V alloy disc (T-4).
Figure 6:
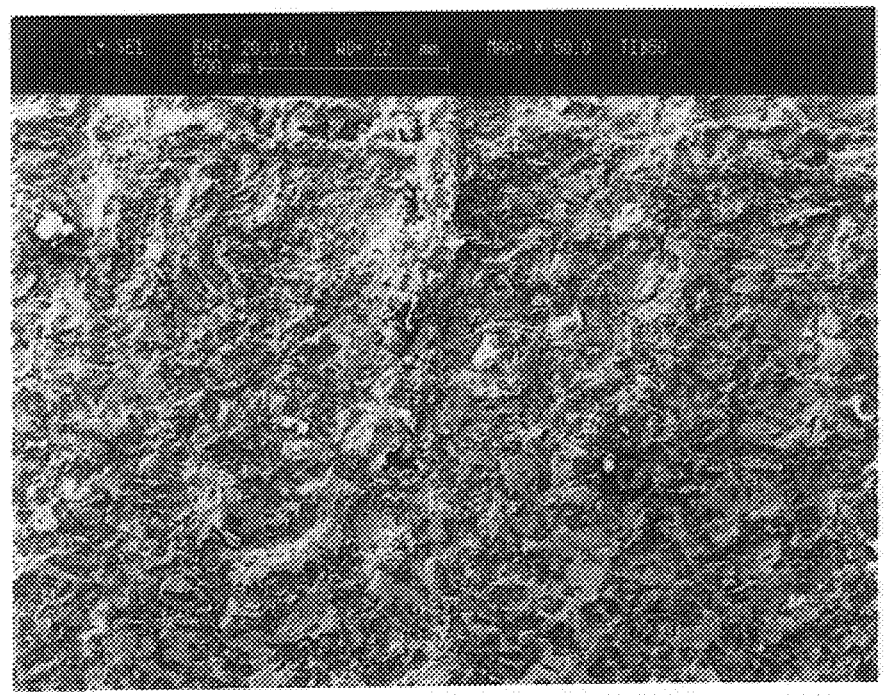
FIG. 6 is a photomicrograph at 50 times magnification of an alumina grit blasted Ti-6Al-4V knee tibial component.
Figure 7:
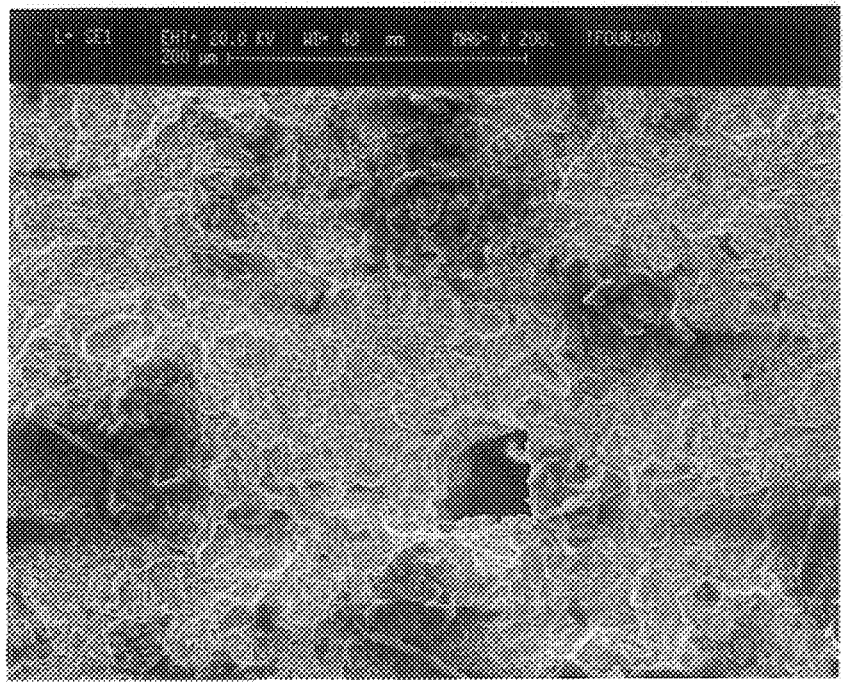
FIG. 7 is a photomicrograph at 200 times magnification of the surface of a water jet blasted Ti-6Al-4V alloy disc (T-4).
Figure 8:
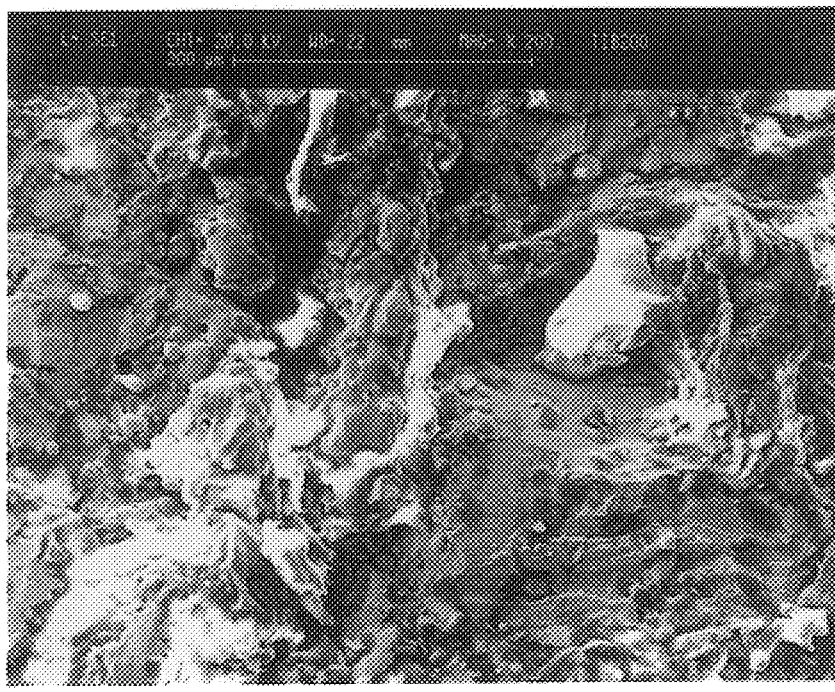
FIG. 8 is a photomicrograph at 200 times magnification of an alumina grit blasted Ti-6Al-4V knee tibial component.
Figure 9:
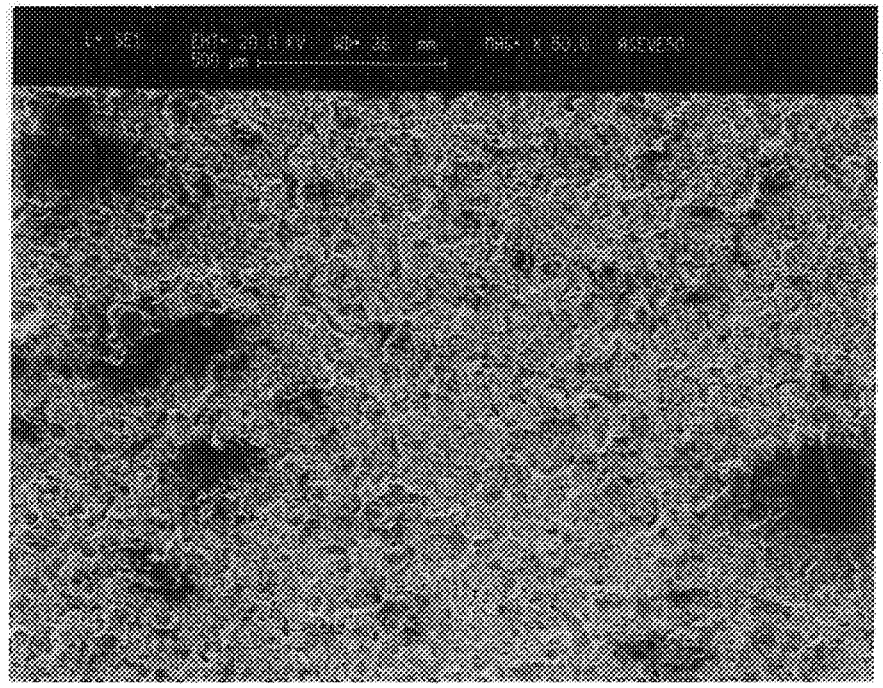
FIG. 9 is a photomicrograph at 50 times magnification of the surface of a water jet blasted aluminum disc (A-7).
Figure 10:
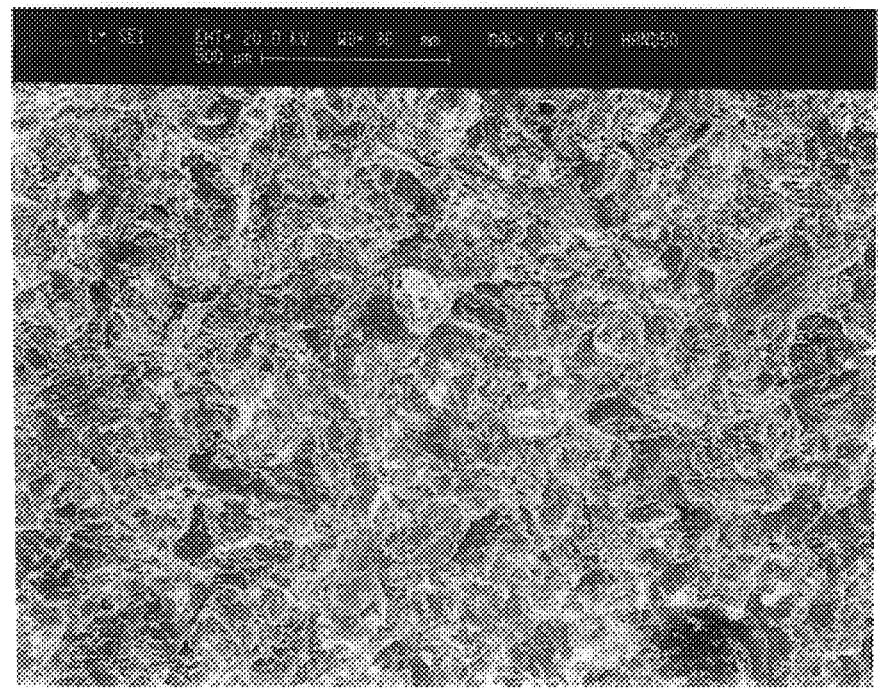
FIG. 10 is a photomicrograph at 50 times magnification of the surface of an alumina grit blasted aluminum instrument handle.
Figure 11:
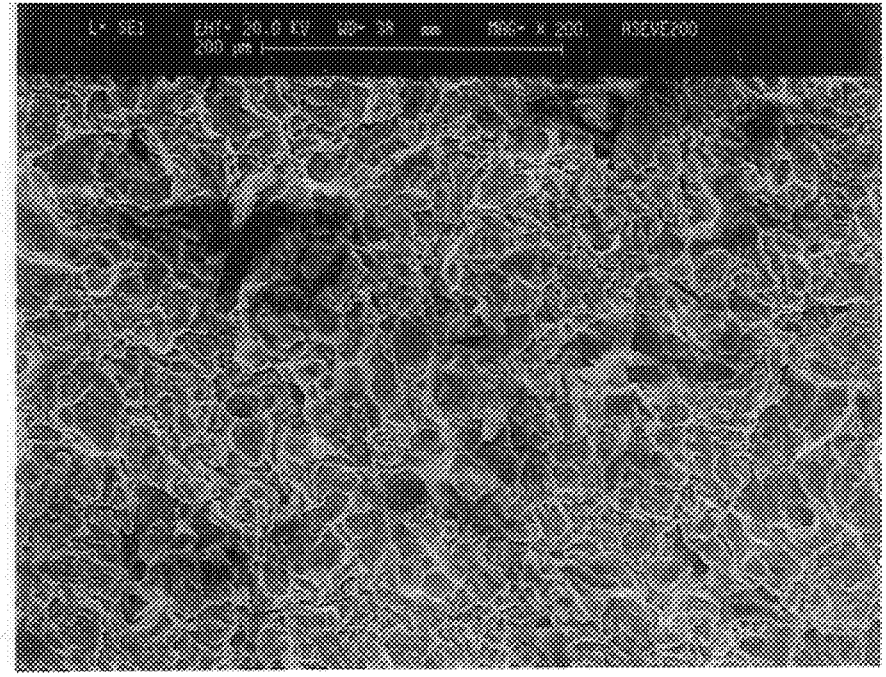
FIG. 11 is a photomicrograph at 200 times magnification of the surface of a water jet blasted aluminum disc (A-7).
Figure 12:
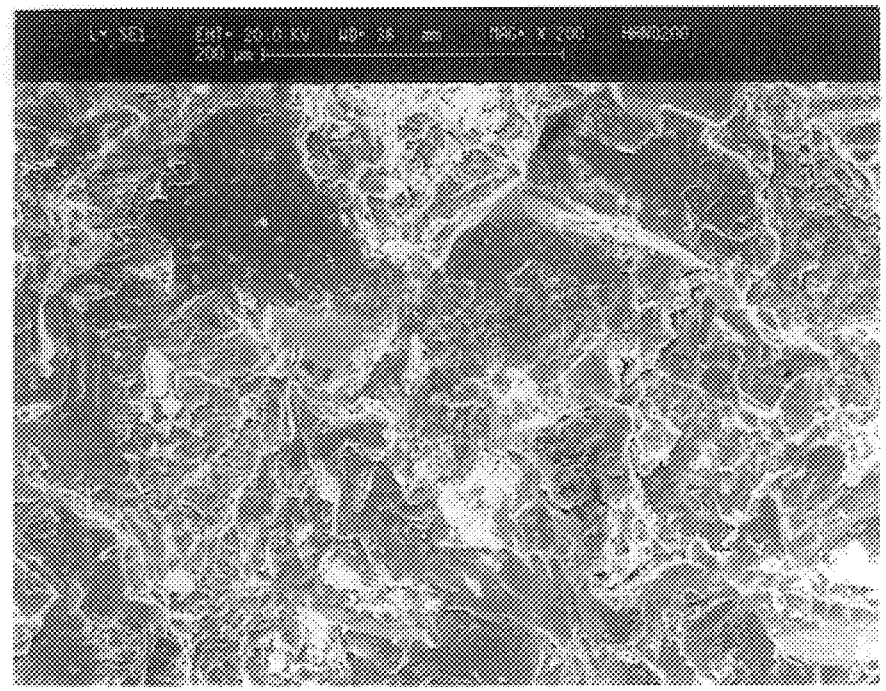
FIG. 12 is a photomicrograph at 200 times magnification of the surface of an alumina grit blasted aluminum instrument handle.

Photomicrographs, at various magnifications, were taken of specimens tabulated in Table 1 for comparison with alumina grit blasted surfaces produced by prior art methods. Thus, FIGS. 1 and 3 are photomicrographs of specimen C-7 that may be compared with alumina grit blasted cobalt-chrome-molybdenum shown in FIGS. 2 and 4. Likewise, FIGS. 5 and 7 are photomicrographs of the surface of specimen T-4 for comparison with alumina grit blasted Ti-6Al-4V shown in FIGS. 6 and 8. FIGS. 9 and 11 are photomicrographs of the surface of specimen A-7 for comparison with alumina grit blasted aluminum surfaces shown in FIGS. 10 and 12. The roughness values of the alumina grit blasted devices were also measured using the same measurement parameters and are given below:

TABLE 2

| Specimen Material | Average Roughness $R_a$(micro inches) | Reduced Peak Height $R_{pk}$(micro inches) | Reduced Valley Depth ($R_{vk}$)(micro inches) |
|---|---|---|---|
| Aluminum | 244 | 252 | 576 |
| Ti-6Al-4V | 250 | 231 | 498 |
| Cast Co—Cr—Mo (ASTM F 75) | 161 | 304 | 351 |
| Cast Co—Cr—Mo (F 75) | 221 | 295 | 108 |
| Cast Co—Cr—Mo (F 75) | 256 | 257 | 206 |
| Cast Co—Cr—Mo (F 75) | 285 | 169 | 517 |
| Wrought Co—Cr—Mo (ASTM F 799) | 196 | 356 | 383 |

EXAMPLE 2

Cylindrical rods of wrought (ASTM F 799) Co-Cr-Mo alloy were subjected to water-jet blasting with a 15° fan jet nozzle at a pressure of 36,000 psi, traverse rate of 0.05 inch/sec and a working distance of 0.375 inch, for approximately 15 passes. The rods were rotated at approximately 11 rpm to ensure uniform texturing of the surface. The roughness values of the specimens were determined by profilometry using the following equipment settings: Trace Length=0.08 inch, Cut-off Length=0.03 inch, Tracing Speed=0.012 inch/sec. The rods were subsequently potted in PMMA bone cement, the cement was allowed to set, and the force required to remove the rods from the cement was measured.

Similar Co-Cr-Mo rods were also subjected to standard alumina grit-blasting, using prior art methods, and their roughness values and cement attachment strength determined, as described above.

The results of both sets of tests are given in Table 3.

TABLE 3

| Blasting Medium | Avg. surface roughness, $R_a$ (micro inches) | Reduced peak height, $R_{pk}$ (micro-inches) | Reduced valley depth, $R_{vk}$ (micro-inches) | Cement attachment Strength (psi) |
|---|---|---|---|---|
| Water-jet | 166 | 96 | 205 | 1595 |
| Water-jet | 176 | 130 | 408 | 1780 |
| Water-jet | 191 | 70 | 365 | 1695 |
| Water-jet | 221 | 156 | 346 | 2027 |
| Water-jet | 227 | 163 | 342 | 1760 |
| Average | 196 ± 27 | 123 ± 40 | 333 ± 76 | 1771 ± 160 |
| Alumina Grit | 151 | 272 | 322 | 1214 |
| Alumina Grit | 154 | 178 | 199 | 1225 |
| Alumina Grit | 167 | 161 | 202 | 1255 |
| Alumina Grit | 187 | 284 | 273 | 1300 |
| Alumina Grit | 149 | 146 | 319 | 1126 |
| Average | 162 ± 16 | 208 ± 65 | 263 ± 60 | 1224 ± 64 |

As shown in the Table, water-jet blasting using the process parameters described above produced a slightly higher cement attachment strength compared to prior art alumina grit blasting. While not wishing to be bound by any theory, the inventors offer the following explanation of this phenomenon. Under certain sets of blasting conditions, the water-jet blasting process can produce smaller, more rounded peaks (smaller Rpk) and larger valleys (greater Rvk) compared to standard grit-blasting, although the overall surface roughness (Ra) may be comparable. This can potentially lead to higher cement attachment strength for water-jet blasted implants, compared to prior-art alumina grit-blasted implants.

Having described the invention above, various modifications of the techniques, procedures, material and equipment will be apparent to those in the art. It is intended that all such variations within the scope and spirit of the appended claims be embraced thereby.

We claim:

1. A method of producing a medical implant having a roughened outer surface suitable for the attachment of tissue, bone, cells or bone cement, the method comprising the step of:
    (a) blasting at least a portion of an outer surface of an implant with a biocompatible liquid free of particulate matter, at a pressure sufficient to produce a roughened outer surface having a roughness profile and a sufficient average surface roughness capable of facilitating the attachment of tissue, bone, cells or bone cement to outer surface of said implant;
    (b) said roughness profile including peaks and valleys about a mean line on the outer surface of said implant, the outer surface of said implant having an average surface roughness of from about 150 micro-inches to about 300 micro-inches wherein said roughened outer surface promotes adhesion of said tissue, bone, cells, or bone cement, introduces residual compression stresses and improves fatigue strength of said medical implant.

2. The method of claim 1, wherein the blasting step is performed at a nozzle pressure of about 36,000 psi and a working distance of about 0.375 inches.

3. The method of claim 1, wherein the biocompatible liquid is water.

4. A method of producing a medical implant with a roughened outer surface suitable for the attachment of tissue, bone, cells, or bone cement, the method comprising the steps of:
    (a) blasting at least a portion of an outer surface of an implant with a blasting medium comprising a biocompatible liquid and biocompatible solid particulates selected from the group consisting of soluble biocompatible salts, deliquescable biocompatible solids, sublimatible biocompatible solids, and vaporizable biocompatible solids at a pressure sufficient to produce a roughened outer surface on said implant having a roughness profile and a sufficient average surface roughness capable of facilitating the attachment of tissue, bone, cells or bone cement to said outer surface of said implant;
    (b) said roughness profile including peaks and valleys about a mean line on the outer surface of said implant, the outer surface of said implant having an average surface roughness of from about 150 micro-inches to about 300 micro-inches; and
    (c) removing substantially all embedded and attached particulate debris left by the blasting medium when blasting said implant in order to provide a roughened outer surface substantially free of embedded and attached particulate debris from the blasting medium wherein said roughened outer surface promotes adhesion of said tissue, bone, cells, or bone cement, introduces residual compression stresses and improves fatigue strength of said medical implant.

5. The method of claim 4, wherein the removing step comprises a step selected from the group consisting of ultrasonic cleaning, flushing with a biocompatible liquid, sublimating said embedded and attached particulate debris and vaporizing said embedded and attached particulate debris.

6. The method of claim 4, wherein the biocompatible solid particulates are soluble biocompatible salts that are soluble in a biocompatible solubilizing liquid, whereby said removing step further includes dissolving embedded and attached particulate debris left by the blasting medium in said biocompatible solubilizing liquid.

7. The method of claim 4, wherein the biocompatible liquid is water and the biocompatible solid particulates are sodium chloride.

* * * * *